United States Patent [19]

Larm et al.

[11] Patent Number: 5,049,403

[45] Date of Patent: Sep. 17, 1991

[54] PROCESS FOR THE PREPARATION OF SURFACE MODIFIED SOLID SUBSTRATES

[75] Inventors: Karl O. P. Larm, Bromma; Lars A. Adolfsson; Kjell P. Olsson, both of Uppsala, all of Sweden

[73] Assignee: Norsk Hydro a.s., Oslo, Norway

[21] Appl. No.: 420,481

[22] Filed: Oct. 12, 1989

[51] Int. Cl.$^5$ .............................................. A01N 1/02
[52] U.S. Cl. ..................................... 427/2; 428/409; 428/410; 428/426; 428/457; 428/421; 428/423.1; 428/447; 428/500; 514/56; 514/59
[58] Field of Search ............ 428/409, 410, 421, 423.1, 428/426, 457, 447, 500; 427/2; 514/56, 59

[56] References Cited

U.S. PATENT DOCUMENTS 4,565,740 1/1986 Golander et al. ............... 428/35.7 X Primary Examiner—Michael Lusignan
Attorney, Agent, or Firm—Wenderoth, Lind & Ponack

[57] ABSTRACT

Method for surface modifying substrates characterized in absorbing on the surface of a solid substrate a polyamine of a high average molecular weight and crosslinking this with crotonaldehyde either simultaneously or by addition in separate steps to produce amino groups on the surface of the substrate, and optionally adsorbing one or several alternating layers of an anionic polysaccharide and of the said polyamine being crosslinked with crotonaldehyde, and optionally finally adsorbing the said polyamine, not cross-linked, to produce free primary amino groups by which chemical entities having a biological activity may be bound by covalent or ionic bonding.

14 Claims, No Drawings

PROCESS FOR THE PREPARATION OF SURFACE MODIFIED SOLID SUBSTRATES

Present invention concerns a process for the preparation of surface modified substrates and the substrates prepared thereby.

TECHNICAL FIELD

It is known that chemical entities having a biological activity may be bound to the surface of a substrate if functional groups are made available on the substrate surface by surface modification. Such functional groups on the substrate surface, may be charged for a ionic interaction or react covalently with functional groups on the chemical entity.

PRIOR ART

The preparation of support matrices for immobilized enzymes by adsorption of a polyamine on a core material and contacting the polyamine with a bifunctional reagent to cross-link and stabilize the polyamine, thus providing a surface with functional groups to which enzymes may be bound covalently has been described a.o. in U.S. Pat. No. 4,268,423 (Rohrbach et al). The cross-linking agent used in this case is chosen from the group consisting of dialdehydes and diisocyanates. In U.S. Pat. No. 4,229,838 (Mano et al) a vascular prothesis having antithrombogenic properties is prepared by adsorbing a special polyamine, polyethylene imine to its porous surface, cross-linking this with a bifunctional agent such as a dialdehyde, and quarternising the remaining amino groups to achieve a positively charged surface on which negatively charged heparin may be adsorbed.

U.S. Pat. No. 4,565,740 (Gölander and Larsson) describes surface modified substrates prepared by adsorbing a complex of a polymeric cationic surfactant, carrying primary as well as secondary and/or tertiary amino nitrogens, preferably polyethylene imine or polyamides, and a dialdehyde, and the dialdehyde having 1-4 carbon atoms between the aldehyde groups, to the surface and eventually adsorbing several additional layers of polymeric anionic surfactants by means of intermediate layers of the complex. To a thus modified surface, a biologically active compound may be adsorbed by ionic binding or bound by covalent binding.

A surface modification should result in a high density of reactive functional groups. Further the reaction should be reproducible and easy to perform under normal reaction conditions, and the modified surface should be stable in the sense that no leakage from the layers of the surface modification should occur.

In practice it has been difficult to prepare surface modified substrates meeting all these requirements in a satisfactory degree with the method according to the last mentioned prior art.

SUMMARY OF THE INVENTION

It has now been found that a surprisingly better surface modification may be achieved by adsorbing a layer of a polyamine having a high average molecular weight on to the surface. The polyamine is stabilised by cross-linking with crotonaldehyde, which is a mono-aldehyde having a C-C double bond in conjugation with the aldehyde function. Thereafter one or more alternating layers of an anionic polysaccharide and the cross-linked polyamine, followed by a final layer of the said polyamine, not cross-linked, may be adsorbed onto the first layer of cross-linked polyamine, whereby a surface modification carrying free primary amino groups is achieved.

DETAILED DESCRIPTION OF THE INVENTION

According to the method of present invention the substrate is brought into contact with an aqueous solution of the polyamine at pH 8-10, especially pH 9. The concentration of the initial polyamine solution will range from 1-10% by weight, especially 5% by weight, 1 ml of which may be diluted to a final volume of 500-2000 ml, especially 1000 ml. This final solution may also comprise from 100-1000 $\mu$l, especially 340 $\mu$l crotonaldehyde. Alternatively the substrate will be treated first with a solution of polyamine of said concentration and pH, and then with a solution of the crotonaldehyde of the said concentration and pH. The temperature is not critical, so it is preferred for the treatment to be at room temperature.

After rinsing with water, the substrate is treated with a solution of an anionic polysaccharide, containing from 10 mg-500 mg, preferably 100 mg, of the polysaccharide in a volume of 1000 ml. This step is executed at a temperature in the range of 40°-70° C., preferably 55° C. and pH 1-5, preferably pH 3.

After another rinsing with water, these first steps may be repeateded one or several times and finally, after having adsorbed a layer of polysaccharide, the substrate may be treated with a polyamine solution having a concentration 1-20 times, preferably 10 times, that mentioned above, at the said temperature and pH.

The polyamine will preferably be a polymeric aliphatic amine, especially polyethylene imine having a high average molecular weight, but any polyamine having a high average molecular weight and carrying free primary amino groups may be used.

The anionic polysaccharide will preferably be a sulfated polysaccharide.

The aminated surface may optionally be further stabilized by reduction with a suitable reducing agent such as sodium cyanoborohydride.

The modified surface according to present invention has free primary amino groups by which chemical entities may be bound either ionically or covalently.

Especially aldehyde containing chemical entities may be bound by formation of Schiff's bases, eventually followed by a stabilization reaction such as a reduction to convert the Schiff's bases to secondary amines.

According to present invention the following advantages are achieved:

A higher density of reactive amino functions resulting in a higher biological activity, when biologically active material is attached.

A significantly lower concentration of cross-linking agent

A very stable final surface

The increased biological activity will appear from the two comparative examples showing the density of binding sites as will appear as the degree of heparinization achieved after the surface modification according to present method and according to the prior art as represented by the working example of U.S. Pat. No. 4,565,740 (Gölander and Larsson):

a) comparing the results achieved when working with, according to present invention, low concentrations of cross-linking agent; and b) comparing the results achieved by these two methods when working with the higher concentrations according to the prior art of crosslinking agent:

Comparative example a)

In these examples tubings of polyethylene (PE) were first etched with potassium permanganate in conc. sulfuric acid, whereafter the tubings were contacted with the following solutions:

1a) 1 ml 5% Polymin SN* and 340 μl crotonaldehyde in 1 l 0.17M borate buffer of pH 9
2a) 1 ml 5% Polymin SN* and 1.54 ml of a solution containing 25% by weight of glutaraldehyde in 1 l 0.17 M borate buffer of pH 9
3) 0.1 g dextran sulphate* in 1l of a 0.15 M sodium chloride solution, pH 3 at 55° C.
4) 10 ml 5% Polymin SN* in 1 l water, pH 9
5) 0.25 g heparin degraded with nitrous acid (as described in U.S. Pat. No. 4,613,665, (Larm)) and 0.025 g sodium cyanoborohydride in 1 l 0.15 M sodium chloride solution of pH 3.9 at 55° C.
6) 0.17 M Borate buffer of pH 9

Polymin SN* is a polyethylene imine commercially available from BASF. The dextran sulphate* used is commercially available from Pharmacia.

The PE-tubings were treated with the different solutions in the following order and rinsed with water between each step: According to present invention: 1a; 3, 1a, 3, 4, 5 and 6. According to the prior art: 2a, 3, 2a, 3, 4, 5 and 6. The tubings were then rinsed with a solution of albumin for 24 hour and the following results were achieved for the heparin activity:

| UPTAKE OF ANTITHROMBIN MEASURED AS THROMBIN INHIBITION IU/cm$^2$ | | |
| --- | --- | --- |
| Cross-linking agent | before rinse | after albumin rinse |
| crotonaldehyde | 27.1 | 20.5 |
| glutaraldehyde | 5.0 | 5.0 |

This shows clearly that a dramatically enhanced heparin activity is achieved by using the method according to present invention with the cross-linking agent according to present invention compared to the cross-linking agent of the prior art when working at the lower concentration according to present invention of the cross-linking agent.

Comparative example b)

The tubings were treated as in example a) except that the solutions 1a and 2a were replaced by 1b and 2b respectively.

1b) 1 ml 5% Polymin SN* and 4.12ml crotonaldehyde in 1l 0.17M borate buffer of pH 9
2b) 1 ml 5% Polymin SN* and 20ml glutaraldehyde (25%-solution) in 1 l 0.17M borate buffer of pH 9

This gave the following results on the heparin activity:

| UPTAKE OF ANTITHROMBIN MEASURED AS THROMBIN INHIBITION IU/cm$^2$ | | |
| --- | --- | --- |
| Cross-linking agent | before rinse | after albumin rinse |
| crotonaldehyde | 9.2 | 7.5 |
| glutaraldehyde | 4.7 | 4.2 |

These results indicate that a surprisingly better activity is also achieved when using the cross-linking agent of present invention at the concentrations of the method of the prior art.

Further, as appears when comparing example a) with example b), it is the combination of the specific cross-linking agent of present invention, namely crotonaldehyde, and the tenfold lower concentration according to the method of present invention that gives the surprisingly higher activity when a biologically active substance is attached to the surface modified according to present invention.

To a surface treated according to present invention, chemical entities carrying functional groups that may react with amino groups without loss of biological activity may be bound. An example of such entities is heparin fragments having aldehyde groups, which are produced by degrading heparin with nitrous acid as described in U.S. Pat. No. 4,613,665 (Larm) for the preparation of heparinized surfaces.

Of course chemical entities other than heparin, having different biological activities and carrying groups that react with amino groups or having been activated to react amino groups, may be bound to the surface by the surface modification according to present invention.

Optionally the free primary amino groups on the surface which are achieved by the final layer of polyamine may be quaternized so that a negatively charged, biologically active compound by be ionically bonded.

As described in the prior art as represented by U.S. Pat. No. 4,565,740, the substrate may be of any material, such as metal especially stainless steel, aluminum, glass or polymeric materials, which are commonly used for the production of medical articles, especially the ones intended for blood contact. Examples of such articles are tubes, catheters, oxygenators, filters, intra vascular probes, blood pumps or the like.

We claim:

1. A method for the surface modification of a substrate which comprises adsorbing on the surface of a solid substrate a polyamine having a high average molecular weight and cross-linking the polyamine with crotonaldehyde.

2. A method according to claim 1 wherein the adsorption and cross-linking with the crotonaldehyde is achieved by applying to the substrate an aqueous solution containing the polyamine and the crotonaldehyde.

3. A method according to claim 1 wherein the polyamine is first adsorbed onto the surface of the substrate and the thus treated substrate is then contacted with a solution containing the crotonaldehyde to achieve cross-linking.

4. A method according to claim 1 wherein following cross-linking there is applied to the substrate a solution of an anionic polysaccharide to obtain at least one adsorbed layer of said anionic polysaccharide.

5. A method according to claim 4 wherein a plurality of adsorbed layers of anionic polysaccharide are formed, each of said layers alternating with an adsorbed layer of the polyamine cross-linked with crotonaldehyde.

6. A method according to claim 1 wherein there is adsorbed onto the treated surface of the substrate as a final step the polyamine which is not cross-linked in order to provide free primary amino groups.

7. A method according to claim 4 wherein there is subsequently adsorbed onto the treated surface of the substrate as a final step the polyamine which is not cross-linked in order to provide free primary amino groups.

8. A method according to claim 6 wherein the free primary amino groups are subsequently quaternized.

9. A method according to claim 7 wherein the free primary amino groups are subsequently quaternized.

10. A method according to claim 1 wherein the substrate is a metal, glass or a polymeric material.

11. A method according to claim 10 wherein the substrate is stainless steel or aluminum.

12. A method according to claim 10, wherein the substrate is selected from polyvinylchloride, polyurethane, silicon rubber, polytetrafluoroethylene, polystyrene and polyolefin.

13. A method according to claim 1 wherein the polysaccharide is dextran sulfate.

14. A method according to claim 1 wherein the polyamine is polyethylenimine.

* * * * *